(12) United States Patent
Moore et al.

(10) Patent No.: US 11,040,340 B1
(45) Date of Patent: Jun. 22, 2021

(54) COLLECTION SYSTEM AND DEVICE FOR REDUCING CLINICAL FALSE POSITIVES AND NEGATIVES IN THE DETECTION OF SARS-COV-2

(71) Applicants: Timothy S. Moore, Newtown, CT (US); Cullen Thomas Moore, Newtown, CT (US)

(72) Inventors: Timothy S. Moore, Newtown, CT (US); Cullen Thomas Moore, Newtown, CT (US)

( * ) Notice: Subject to any disclaimer, the term of this patent is extended or adjusted under 35 U.S.C. 154(b) by 0 days.

(21) Appl. No.: 17/173,149

(22) Filed: Feb. 10, 2021

Related U.S. Application Data

(62) Division of application No. 16/997,850, filed on Aug. 19, 2020, now Pat. No. 10,967,368.

(51) Int. Cl.
| | | |
|---|---|---|
| *C12Q 1/70* | (2006.01) | |
| *C12Q 1/6848* | (2018.01) | |
| *B01D 15/18* | (2006.01) | |
| *G01N 1/10* | (2006.01) | |
| *B01L 1/00* | (2006.01) | |
| *G01N 33/569* | (2006.01) | |
| *G01N 33/53* | (2006.01) | |
| *B01L 3/00* | (2006.01) | |
| *G01N 30/72* | (2006.01) | |

(52) U.S. Cl.
CPC ............... *B01L 1/52* (2019.08); *B01D 15/18* (2013.01); *B01L 3/508* (2013.01); *C12Q 1/6848* (2013.01); *C12Q 1/70* (2013.01); *G01N 1/10* (2013.01); *G01N 30/7233* (2013.01); *G01N 33/5306* (2013.01); *G01N 33/56983* (2013.01); *B01L 2200/141* (2013.01); *B01L 2200/18* (2013.01); *B01L 2300/0609* (2013.01)

(58) Field of Classification Search
CPC ...... B01L 1/52; B01L 3/508; B01L 2200/141; B01L 2300/0609; B01L 2200/18; G01N 33/56983; G01N 33/5306; G01N 30/7233; G01N 1/10; C12Q 1/70; C12Q 1/6848; B01D 15/18
See application file for complete search history.

(56) References Cited

U.S. PATENT DOCUMENTS 8,071,309 B2 * 12/2011 Ecker ..................... G01N 23/00
435/6.12

* cited by examiner

*Primary Examiner* — Jennifer Wecker
*Assistant Examiner* — Michael Paul Shimek
(74) *Attorney, Agent, or Firm* — Withers Worldwide

(57) ABSTRACT

In embodiments there is described a method for reducing false positives and negatives in the detection of SARS-CoV-2 in suspected patients using mass spectroscopy employing the steps of mixing samples of collected saliva and nasopharyngeal secretions in a single sample container; adding universal transport medium to the mixed samples in said single sample container; transporting the single sample container at a temperature above 0° C. to a remote location; deactivation of viral content of the mixed sample; protein digestion of the mixed sample; concomitant separation of peptides, ionization by mass spectroscopy of the separated peptides, and comparison of peptide patterns to known SARS-CoV-2 peptides. Also set forth in an embodiment is a collection container for collecting saliva and/or sputum, as well as a swab member, with universal transport medium and/or virus inactivating agent housed in separate compartment communicable with sample compartment through a one-way valve.

20 Claims, 1 Drawing Sheet
Specification includes a Sequence Listing.

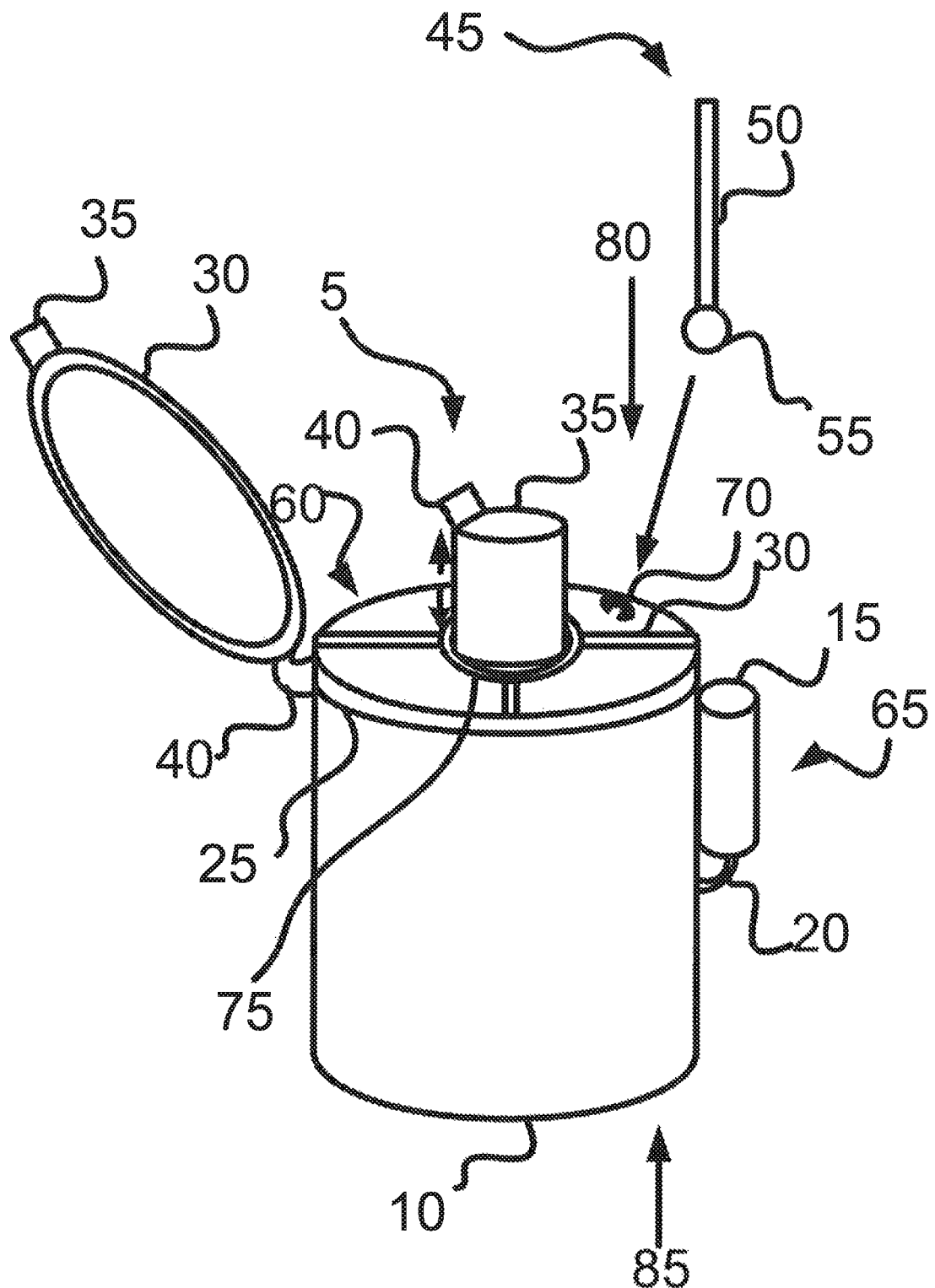

US 11,040,340 B1

COLLECTION SYSTEM AND DEVICE FOR REDUCING CLINICAL FALSE POSITIVES AND NEGATIVES IN THE DETECTION OF SARS-COV-2

CROSS REFERENCE TO RELATED APPLICATIONS

The present application is a divisional of U.S. patent application Ser. No. 16/997,850 filed Aug. 19, 2020.

STATEMENT REGARDING SEQUENCE LISTING

The sequence listing associated with this application is provided in text format in lieu of a paper copy and is hereby incorporated by reference into the specification. The name of the text file containing the sequence listing is CTM104-DIV-SEQ-01.txt. The text file is 2 KB; was created on Mar. 31, 2020; and is being submitted via EFS-Web with the filing of the specification.

TECHNICAL FIELD

The present invention in an embodiment relates to method for reducing false positives and negatives in the detection of SARS-CoV-2 in suspected patients using mass spectroscopy employing the steps of mixing samples of collected saliva and nasopharyngeal secretions in a single sample container; adding universal transport medium to the mixed samples in said single sample container; transporting the single sample container at a temperature above 0° C. to a remote location; deactivation of viral content in in the sample container; protein digestion of the mixed sample; concomitant separation of peptides, ionization by mass spectroscopy and comparison of peptide patterns to known SARS-CoV-2 peptides. Also set forth in an embodiment is a collection container for collecting saliva and/or sputum, as well as a swab member, with universal transport medium and/or virus inactivating agent housed in separate compartment communicable with sample compartment through a one-way valve. Analysis of samples is for bat-specific SARS-Cov-2 nucleopeptide sequences found predominantly in saliva and/or sputum but not in nasopharyngeal specimens, as well as nucleopeptide sequences found predominantly in nasopharyngeal specimens but not in saliva and/or sputum samples. A positive finding of infectivity is declared upon detection of amino acid sequences of at least one of: ADETQALPQR (SEQ. ID NO.: 1), DGIIWVATEGALNTPK (SEQ. ID NO.: 2), IGMEVTPSGTWLTYTGAIK (SEQ. ID NO.: 3), WYFYYLGTGPEAGLPYGANK (SEQ. ID NO.: 4) and RPQGLPNNTA SWFTALTQHG (SEQ. ID NO.: 5). In a more preferred embodiment, when either of SEQ. ID NO.: 1 and SEQ. ID NO.: 5 are found, but not both, SARS-CoV2 testing is re-performed by mass spectrometry or other method before a positive result is reported. A negative finding of infectivity is declared upon failure to detect peptide sequences of at least one of: SEQ. ID NO.:1-5. In a preferred embodiment, before ionization saliva and/or sputum and nasopharyngeal specimens are pooled from 5 or less persons in order to improve the speed of analysis by mass spectroscopy of overall samples. Individual analysis of each specimen making up the pool is performed only if the pooled sample is found to be positive for SARS-CoV-2 by detection of at least one of SEQ. ID NO.:1-5.

BACKGROUND

A new coronavirus, designated SARS-CoV-2, has ravaged the world since December 2019. This virus first jumped into humans in Wahun, Hubei Province, China, and then quickly spread across the world. SARS-CoV-2 had never before the infections in China been reported in humans. On Jan. 31, 2020, the Secretary of HHS issued a declaration of public health emergency related to COVID-19. On Mar. 11, 2020 the WHO declared the outbreak of SARS-CoV-2 to be a pandemic. It is estimated that somewhere around 20 percent of infected individuals may develop serious consequences. It is believed that the main cause of transmission is by respiratory droplets, albeit other routes have been hypothesized such as direct human to human contact and fecal to oral contamination. The incubation period of the disease is believed to be 14 days.

Coronaviruses (CoVs) are among the largest known group of viruses in the family Coronaviridae and order Nidovirales. SARS-CoV-2 belong to the Betacoronavirus genus. It has a genome size of approximately 30 kilobases, and is Baltimore class IV positive-sense single-stranded RNA virus. Four structural proteins are encoded in the RNA, spike (S) protein, envelope (E) protein, membrane (M) protein, and nucleocapsid (N) protein. Betacoronaviruses are spherical or pleomorphic in shape having an average diameter of about 125 nm.

On Feb. 4, 2020, the Human Health and Services Secretary determined that there was a public health emergency and therefore emergency use authorization (EUA) would be put into place for in vitro diagnostics for the detection and/or diagnosis of SARS-CoV-2. The FDA's EUA templates require only analytic sensitivity and specificity of analysis. Analytical sensitivity is the smallest amount of substance in a sample that can be reliably detected by an assay (limit of detection) while analytical specificity is the assay's ability to detect only the desired substance without cross reacting with other substances. The Food and Drug Administration requires 95% positive and negative agreement with a reference sample for a laboratory-developed test to be acceptable in a molecular diagnostic for a pathogen, such as SARS-CoV-2. These parameters do necessarily result in an equivalent clinical sensitivity and specificity. Indeed, many clinically se positives and negatives are being uncovered with currently employed SARS-CoV-2 detection tests. Over 45 commercial COVID-19 test kits, and 10-laboratory developed tests had received FDA EUA approval by Apr. 24, 2020.

Molecular tests for SARS-CoV-2 presently are primarily based on reverse transcription-quantitative polymerase chain reaction (RT-qPCR) on cell-free fluid samples of respiratory tract specimens. RT-PCR analysis involves the reverse transcription of SARS-CoV-2 RNA into complementary DNA (cDNA) strands, followed by amplification of specific regions of the cDNA. The CDC test presently available measures the rate of florescent signal accumulation as a surrogate for direct nucleic acid determination. The gene target for the US CDC, National Institute of Infectious Diseases Japan, and the National Institute of Health, Thailand is the N gene, while the China CDC looks at a combination of ORF lab and the Ngene.

Other less widely used techniques are also available.

Immunofluorescence assays make use of fluorescently tagged antiviral antibodies to detect viral antigens, with the amount of binding of the antibody being directly correlated with the amount of florescence produced. Nucleocapsid protein of SARS-CoV-2 has been detected by fluorescence immunochromatography. See, Diao, et al., *Diagnosis of Acute Respiratory Syndrome Coronavirus 2 Infection by Detection of Nucleocapsid Protein*, medRxiv preprint Mar. 13, 2020 at https://doi.org/10.1101/2020.03.07.20032524.

Enzyme-linked immunosorbent assays (ELISA) are also used for detection of SARS-CoV-2. In such testing antibodies specific to viral antigens are bound to a plastic surface and the sample overlaid. If the sample contains viral antigens it results in a positive reaction detectable by the marker changing color when an appropriate solution is added. Antibodies of SARS-CoV-2 that have been used in ELISA detection kits include spike antibody, envelope antibody, membrane antibody and nucleocapsid antibody.

Other biological techniques that are in development include molecularly imprinted polymer-based detection, aptamer-based detection, and CRISPR-Cas 12-based lateral flow detection of RNA extracts of SARS-CoV-2. Broughton, et al., *CRISPR-Cas12 based detection of SARS-CoV2*, Nature Biotechnology 38, 870-874 (Apr. 16, 2020). The CRISPR-Case 12 assay performs simultaneous reverse transcription and isothermal amplification using loop-mediated amplification (RT-LAMP) for RNA extracted from samples followed by Cas12 detection of predefined coronavirus sequences, after which cleavage of a reporter molecule confirms detection of the virus.

Mass spectrometry (MS) is a sensitive technique used to detect, identify and quantitate molecules based on their mass-to-charge (m/z) ratio. Originally developed almost 100 years ago to measure elemental atomic weights and the natural abundance of specific isotopes, MS was first used in the biological sciences to trace heavy isotopes through biological systems. In later years, MS was used to sequence oligonucleotides and peptides and analyze nucleotide structure.

MS has been used for the identification of peptides. Peptide mass fingerprinting is performed by using the masses of proteolytic peptides to search a database of predicted masses that should arise from the digestion of certain proteins. Mass spectrometry of proteins requires that proteins in solution or solid state be turned into an ionized form in a gas phase before injection and acceleration in the electric or magnetic field for analysis. Two primary methods of protein ionization are used, that is, electrospray ionization (ESI) and matrix-assisted laser desorption/ionization (MALDI).

Tandem mass spectrometry (MS/MS) is frequently used in peptide and protein analysis. See, Trauger et al., *Peptide and protein analysis with mass spectrometry*, Spectroscopy 16: 15-28 (2002). In such approach, distinct ions of interest are in a quadrupole filter based on their m/z during the first round of MS and are fragmented by a number of different dissociation methods (such as colliding the ions with a stream of inert gas, also known as collision-induced dissociation (CID) or higher energy collision dissociation (HCD), or electron-transfer dissociation (ETD) and electron-capture dissociation (ECD)). In the second round of MS, the fragments are separated based on their individual m/z ratios. Comparison of the spectra is made to patterns stored in databases such as IPI, REfSeq and UniProtKB/Swiss-prot. The most widely used instrument for peptide mass analysis are the MALDI-TOF instruments as they permit the acquisition of peptide mass fingerprints (PMFs) at a high pace. The sensitivity of current mass spectrometers allows one to detect analytes at concentrations in the attomolar range ($10^{-18}$).

Before MS identification can be performed peptides must be separated from one another to allow for single peptide analysis. Preparation includes removal of detergents and reduction in the complexity of the sample by, for example, lysate preparation and protein digestion. Proper sample preparation is critical for MS analysis, because the quality and reproducibility of sample extraction and preparation significantly impact results from MS instruments.

Gas chromatography (GC) and liquid chromatography (LC) are common methods of pre-mass spectrometry separation. With LC-MS, electron spray ionization (ESI) is commonly applied, resulting in the production of aerosolized ions. On the other hand with GC-MS, the sample may be ionized directly or indirectly via ESI. The development of macromolecule ionization methods, including electrospray ionization (ESI) and atmospheric pressure chemical ionization (APCI), enabled the study of protein structure by MS.

Typically a sample is digested with proteolytic enzyme resulting in a complex mixture of proteins. Next, the digested sample is chromatographically separated in one or multiple dimensions and introduced to the mass spectrometer, for example, by nanoflow high-performance liquid chromatography (nHPLC) column integrated directly to an ESI source on the mass spectrometer. The ESI source then converts condensed phase ions eluting from the HPLC column, to multiply protonated molecules in the gas phase.

High performance liquid chromatography (HPLC) is likely the most common separation method to study biological samples by MS or MS/MS (termed LC-MS or LC-MS/MS, respectively), because the majority of biological samples are liquid and nonvolatile. LC columns have small diameters (e.g., 75 μm; nanoHPLC) and low flow rates (e.g., 200 nL/min), which are ideal for minute samples. Additionally, "in-line" liquid chromatography (LC linked directly to MS) provides a high-throughput approach to sample analysis, enabling the elution of multiple analytes through the column at different rates to be immediately analyzed by MS. For example, 1 to 5 peptides in a complex biological mixture can be sequenced per second by in-line LC-MS/MS.

All mass spectrometers have an ion source, a mass analyzer and an ion detector. Samples are loaded into the mass spectrometer in liquid, gas or dried form and then vaporized and ionized by the ion source (e.g., APCI, DART, ESI).

The charge on the molecules by the ionizer allows the mass spectrometer to accelerate the ions through the remainder of the system. Ions come into contact with electric and/or magnetic fields from the mass analyzer deflecting the ions based on their m/z. Commonly employed mass analyzers include ion traps, orbitraps, time-of-flight (TOF), and quadrupoles. The ions that have successfully been deflected by the mass analyzer then hits the ion detector. The mass spectrometer then records the mass/charge (m/z) of each peptide ion and then selects the peptide ions individually to obtain sequence information via, for example, MS/MS. Conventionally the process is performed under an extreme vacuum of $10^{-6}$ to $10^{-8}$ torr to remove gas molecules and neutral and contaminating non-sample ions. Mass spectrometers are connected to computer-based software platforms that measure ion oscillation frequencies and acquire mass spectra using image current detection. Data analysis programs detect ions and organize them by their individual m/z values and relative abundance. These ions can then be identified via established databases that predict the identity of the molecule based on its m/z value.

While RT-qPCR tests are still consider the gold standard of testing for SARS-CoV-2 infectivity, a number of researchers have reported both false positives and negatives when automated full DNA sequencing is not used. The CDC RT-qPCR assay panel uses TaqMan probes to bind to only 2 or 3 target nucleotide sequences if such are present in the sample. The probes are labeled with a fluorescent dye reporter at the 5' end and a quencher at the 3' end. The 5'-3' exonuclease activity of Taq polymerase is used to cleave and degrade the dual-labeled probes which have annealed to the complementary target sequences during hybridization. Degradation of the probe releases the fluorophore from it and breaks its proximity to the quencher, thus relieving the quenching effect and allowing fluorescence of the fluorophore.

In an article by Sin Hang Lee, *Test for SARS in cellular components by routine nested RT-PCR followed by DNA Sequencing*, Int. J. Ger. & Rehab. 2(1):69-96 (Jul. 17, 2020), the author found that 10 samples out of 20 samples classified as negative, 2 were actually positive when a 398-bp heminested PCR amplicon was used as a template for direct DNA sequencing (each patient was found to have a novel single nucleotide insertion in the N gene). Likewise, out of the 10 originally classified as positive, three were found to be actually negative (that is, a 30% false positive rate and a 20% false negative rate). Yang et al., *Viral RNA level, serum antibody responses, and transmission risk in discharged COVID-19 patients with recurrent positive SARS-CoV-2 RNA test results: a population-based observational cohort study*, medRXiv Jul. 26, 2020, doi: https//doi.prg/10.1101/2020.07.21.20125138, attribute false positives as being due to the presence of low levels of viral RNA fragments and not the shedding of infectious virus particles.

No mass spectrometry test method for SARS-CoV-2 diagnosis has yet received EUA approval. However, the detection of SARS-CoV-2 by mass spectroscopy has been recently proposed by a few groups. See, Cardozo, et al., *Fast and low-cost Detection of SARS-CoV-2 Peptides by Tandem Mass Spectrometry in Clinical Samples*, May 17, 2020 Research Square DOI: 10.21203/rs.3.rs-28883/v1; Nikolaev, et al., *Mass Spectrometric Detection of SARS-CoV-2 Virus in Scrapings of the Epithelium of the Nasopharynx of Infected Patients Via Nucleocapsid N Protein*, bioRxIV preprint, at https//doi.org/10.1101/2020, 05.24.113043, posted May 25, 2020; Ihling et al., *Mass Spectrometric Identification of SARS-CoV-2 Proteins from Gargle Solution Samples of COVID-19 Patients*, Proteome, Jun. 22, 2020 at https://dx.doi.org/10.1021.acs.jproteome.0C00280; Gouveia et al., *Proteotyping SARS-CoV-2 Virus from Nasopharyngeal Swabs: A Proof-of-Concepts Focused on a 3 Min Mass Spectrometry Window*, Jul. 22, 2020 at https;//dx-.doi.org/10.1021/acs.jproteome.0c00535.

The present inventors have noted a deficiency in each proposed mass spectrometry system reported to date in that each depends on analysis of samples from a single corporal source situs. Three of such proposed analysis systems use only samples from the nasopharynx region of the body, while one uses a gargle sample obtained by swishing the liquid through the whole mouth and gargling the same.

The present inventors note that antigens associated with a specific pathogen may or may not be detectable in different biological samples obtained from different corporal sources, such as blood, urine, sweat, saliva or nasal secretions, at any particular time point. They have recognized that clinically false positive and negatives can be dramatically reduced by testing for a pathogen, particularly SARS-CoV-2, by analyzing concurrently multiple distinct corporally obtained samples known to be associated with a prominent situs of pathogen entry and/or exit. They set forth herein a method of collecting and processing multiple samples obtained from clinically distinct sites in the body in conjunction with one another and in the concomitant preparation of the peptide libraries for mass spectrometry analysis.

Wang et al., *Detection of SARS-CoV-2 in Different Types of Clinical Specimens*, JAMA 323(18):1843-1844 (May 12, 2020)(published on line Mar. 11, 2020) report that in a study of 1070 specimens collected from 205 patients with COVID-19, dramatic differences were seen in positive rates of infectivity based on rRT-PCR (targeting the open reading frame lab gene) depending on the biological sample analyzed. While bronchoalveolar lavage fluid specimens were found to elicit a positive result in 93 percent of patients from which such samples were taken (14), sputum elicited a positive response in 72% of patients (72 out of 105), and nasal swabs elicited a positive response in 63% of patients (5 out of 8), all other samples taken from other bodily sites provided less than 50% positivity—biobronchoscope brush biopsy (46%: 6 out of 13), pharyngeal swabs (32%—126 out of 398), feces (29%—44 out of 152), blood (1%—3 out of 307) and urine (0%—out of 72 tested). In another study performed at a different hospital (Guangzhou Medical University), looking at 16 critically ill patients with COVID-19 (using a RT-PCR assay looking at two target genes, ORF lab (open reading frame lab) and N (nucleocapsid protein)), the authors found throat swabs to demonstrate 63% positivity (10/16), nasal swabs to provide for 80% positivity (13/16) and sputum/endotracheal aspirate (ETA) 100% positivity, while each of urine, blood, conjunctival, and anal swabs showed less than 50% positivity.

The present inventors have recognized that in regard to SARS-CoV-2 false negatives may be a result of limiting analysis to only samples sourced from one clinical site within the human body as the duration of shedding from different clinically different bodily sites may be significantly different from one another. They note that in a study by 30 patients by Wang et al., *Differences of SARS-CoV-2 Shedding Duration in Sputum and Nasopharyngeal Swab Specimens Among Adult Inpatients with COVID-19*, Chest prepublication Jul. 3, 2020, 2-9, that 14 patients who were positive for SARS-CoV2-RNA (using rRT-PCR assay as well as antibody detection) did not demonstrate positivity in both nasopharyngeal samples (NPS) and sputum (SP) samples, but rather only in one or the other samples. Furthermore, in the 16 cases wherein positivity was noted both in NPS and SP samples, nine patients had positive testing for SARS-CoV-2 RNA in the sputum after NPS turned negative, six patients had positive sputum before NPS turned negative, and one patient had positive sputum on the day when NPS turned negative. In short, the study found that median duration of SARS-CoV-2 from sputum was significantly longer than from NPS. As noted by the present inventors all patients would have been found positive over the analysis period if testing was performed on samples from each clinically separate bodily sample (that is, NPS and SP).

The present inventors have recognized that nucleoprotein fingerprinting has a number of advantages over nucleic acid detection techniques, in particular sequencing that using less than 398-bp hemi-nested PCR amplicon as template for direct DNA sequencing. First, nucleoprotein MS sequencing does not employ amplification. With rRT-PCR small samples of nucleic acid residues may be found to be indicative of an active viral infection via amplification when such are just by product of a prior infection. Nucleoprotein concentration will naturally reduce when an infection is complete and a negative finding of the same means the infection has passed. Second nucleoprotein fingerprinting is robust in that many peptide fragments may be monitored for at the same time. By using samples from biological locations with distinct nucleoprotein profiles, such as seen in saliva and the nasopharynx, one can get a much better understanding of whether the viral disease is active or not. Lastly, the present inventors note that nucleoprotein fingerprinting holds a further advantage in that nucleoproteins transport also does not require dry ice shipment as associated with non-dried or pretreated RNA samples for analysis. In fact, they are generally stable at room temperature.

Saliva means the clear slightly alkaline liquid secreted into the mouth by the salivary glands and mucous glands, and consists of water, mucin, protein and enzymes. Sputum on the other hand means matter coughed up and expectorated from the mouth, and comprises both saliva and discharges from the respiratory passages such as mucus, phlegm or pus. The mean value of the RESID plus volume normally swallowed in males is about 1.2 ml and females 0.96 ml. Therefore sample containers should have the ability to hold somewhere between 0-5 ml of saliva. See, Lagerlof et al., *The volume of saliva in the mouth before and after swallowing*, J. Dent. Res. 63(5): 618-21 (1984).

The present inventors have recognized that saliva and sputum have many of the same nucleoproteins of SARS-CoV-2 in them. The importance of the same is that saliva is generally much easier to garner from patients. It is reported by at least one group that 72% of COVID-19 patients were not able to produce sputum for collection. Huang et al., *Clinical features of pateints infected with 2019 novel coronavirus in Wuhan, China*. Lancet 395:497-506 (2020). The salivary gland is believed to be a reservoir harboring the latent infection. In fact, it has been shown that ACE2 epithelial cells of the salivary glands can be the initial target for SARS-CoV in rhesus monkeys. Liu et al., *Epithelial cells lining salivary gland ducts are early target cells of severe acute respiratory tracts of rhesus macaques*. J. Virol. 85: 4025-30 (2011).

Studies have shown that saliva at least in regard to RNA detection is somewhat lower in sensitivity than nasopharyngeal swabs. Jamal, et al., *Sensitivity of nasopharyngeal swabs and saliva for the detection of severe acute respiratory syndrome coronavirus 2 (SARS-CoV-2)*, medRxiv, May 5, 2020 at https://doi.org/10.110/2020.05.01.20081026, report a sensitivity of about 89% for nasopharyngeal swab detection, with 72% for saliva based on 91 patients (indicating NP swabs being 17% more sensitive than saliva at the time point measured—with only 6% difference at week 1 and a 20% difference at week 2 or later). Azzi et al., *Saliva is a reliable tool to detect SARS-CoV-2*, J. Infect. PubMed PMID:32298676 (Apr. 14, 2020), on the other hand, found among 76 patients with 10 patients having COVID-19 that the concordance rate between both samples was about 97% again using RT-qPCR.

The present inventors have recognized that in mixing samples obtained from the nasopharynx and those from saliva, that the mixed sample provides significantly better clinical detection of SARS-CoV-2 infectivity than analysis of either sample alone, significantly reducing false negatives. They have also recognized that false negatives can be reduced by mixing further samples wherein SARS-COV-2 has been found to be prominent in the sample, such as bronchoalveolar lavage fluid or throat swab. On the other hand, the use of protein analysis via mass spectrometry greatly reduces false positives seen in RT-PCR due to amplification of residual RNA that is associated with dead viral components. The inventors have also recognized false positives may also be reduced when positive/negative findings of peptides of prominent active infection in two different clinical samples do not correlate. In such case, rerunning analysis may further reduce false positives.

SUMMARY

Accordingly, the present invention in an embodiment relates to a method for reducing clinical false positives and negatives in the detection of SARS-CoV-2 in suspected patients by using mass spectroscopy employing the steps of mixing samples of collected saliva and nasopharyngeal secretions in a single sample container; adding universal transport medium to the mixed samples in said single sample container; transporting the single sample container at a temperature above 0° C. to a remote location; deactivation of viral content of the mixed sample; protein digestion of the mixed sample; concomitant separation of peptides, ionization by mass spectroscopy of the separate peptides, and comparison of peptide patterns to known SARS-CoV-2 peptides. Preferred analysis of samples is for bat-specific SARS-Cov-2 nucleopeptide sequences found predominantly in saliva and/or sputum but not in nasopharyngeal specimens, as well as nucleopeptide sequences found predominantly in nasopharyngeal specimens but not in saliva and/or sputum samples. A positive finding of infectivity is declared upon detection of amino acid sequences of at least one of: ADETQALPQR (SEQ. ID NO.: 1), DGIIWVATEGALNTPK (SEQ. ID NO.: 2), IGMEVTPSGTWLTYTGAIK (SEQ. ID NO.: 3), WYFYYLGTGPEAGLPYGANK (SEQ. ID NO.: 4) and RPQGLPNNTA SWFTALTQHG (SEQ. ID NO.: 5). In a more preferred embodiment, a positive finding of infectivity is not declared if one but not both of SEQ. ID NO. 1 and SEQ. ID No. 5 are detected. In such case, analysis is repeated or another SARS-CoV-2 test is employed before declaring a positive result. A negative finding of infectivity is declared upon failure to detect peptide sequences of at least one of: SEQ. ID NO.:1-5. In a preferred embodiment, before ionization saliva and/or sputum and nasopharyngeal specimens are pooled from 5 or less persons in order to improve the speed of analysis by mass spectroscopy of overall samples. Individual analysis of each specimen making up the pool is performed only if the pooled sample is found to be positive for SARS-CoV-2 by detection of at least one of SEQ. ID NO.:1-5.

Also set forth in an embodiment is a collection container for collecting saliva and/or sputum, as well as a nasopharyngeal swab member, with universal transport medium and/or virus inactivating agent housed in separate compartment communicable with sample compartment through a one-way valve.

BRIEF DESCRIPTIONS OF THE DRAWINGS

FIG. 1 is a perspective view of a container apparatus according to a preferred embodiment of the invention for collection of sputum and receipt of a swab.

DESCRIPTION OF SPECIFIC EMBODIMENTS

In one embodiment there is provided a method for reducing clinical false positives and negatives in the detection of SARS-CoV-2 in suspected patients employing the steps of: (a) mixing in a single sample container samples of collected saliva and nasopharyngeal secretions to form mixed samples; (b) adding universal transport medium to the mixed samples in said single sample container to form treated mixed samples; (c) transporting at a temperature above 0° C. the single sample container having the treated mixed samples to a remote location; (d) treating at such remote location the treated mixed sample to deactivate live viral content; (e) digesting the peptides found in the deactivated treated mixed sample to form a digested sample; (f) separation of each of the peptides in the digested sample, (g) ionization of the separated peptides by mass spectroscopy; and (h) comparison of peptide patterns obtained by mass spectroscopy to known SARS-CoV-2 nucleocapsid peptides associated with SARS-CoV-2. A further stop (h) may be employed wherein comparison is made to each of the following nucelocaspid peptides: ADETQALPQR (SEQ. ID NO.: 1), DGIIWVATEGALNTPK (SEQ. ID NO.: 2), IGMEVTPSGTWLTYTGAIK (SEQ. ID NO.: 3), WYFYYLGTGPEAGLPYGANK (SEQ. ID NO.: 4) and RPQGLPNNTA SWFTALTQHG (SEQ. ID NO.: 5). In a further step (i) declaration that the patient is infected with SARS-CoV-2 is made if any of the peptide patterns found match any of SEQ. ID Nos. 1-5, and not infected if none of the peptide patterns found match any of SEQ. ID Nos. 1-5. In a more preferred method if the determinations of both SEQ. ID No. 1 and 5 do not match, the sample is reanalyzed for SARS-Cov-2 infectivity by mass spectrometry or another method before a positive result is called. In a more preferred method, the mixed sample also comprises one of at least one of: a sputum sample, a bronchoalveolar lavage fluid sample, a throat swab sample and a fibrobronchoscope brush biopsy. Preferably each of said samples should be interrogated to determine predominant peptide sequences that differ from all other clinical samples to be added into the mix, and such determine peptide sequences should be used in the screen along with the such other peptides.

A preferred mass spectrometer of step (g) used to ionize the separated peptides is the triple quadrupole mass spectrometer. It is also preferred that separation of digested peptides of step (f) be performed using 4 channel turbulent flow chromatography.

In order to increase speed of analysis, when the expected positivity rate is ten percent or less, pools of mixed samples for 5 or less patient groups maybe analyzed first. In such case, those pooled samples of 5 patients that are not positive save 4 analyses. For those pools that are positive, one additional analysis would need to be made, as each sample would then have to be analyzed separately that make up the positive pool of 5 patients. In any case, the number of samples needed to be analyzed is dramatically reduced when positivity is believed to as low as 10-15% in the sample that must be tested.

There is also disclosed a collection container for collecting saliva and/or sputum samples and specimens from a swab, such as a nasopharyngeal swab. The collection container comprises: (a) a container body having an open top portion and a closed bottom portion, and sidewalls encompassing a sample void, said container defined circumferentially about an axis; (b) a band of material circumferential about the sidewalls of said container body at the open top portion of said container along the outside of said sidewalls as adjudge from said container body axis; (c) a cover configured to be coupled to the top portion of the container body to close the container, said cover joined to said container body by a flexible joint adjoined to said band of material; (d) a circumferential ring about said container body axis surrounding a hole, said circumferential ring joined to the sidewalls of said container body by one or more struts; (e) a straw in said circumferential band hole, said straw movable between a position above said top portion of said container body and a position substantially parallel to the top portion of said container body; (f) a tab extending from said straw to allow a grasping surface to pull said straw up through the circumferential band hole and to push down said straw into said hole to a position wherein the top of the straw is substantially parallel to the top portion of said container body; (g) a flexible container affixed to the outer side wall of the container body as adjudged from said container body axis, said flexible container containing liquid; (h) a conduit attached to said flexible container, said conduit leading the sample void and having a one-way valve to allow liquid in said flexible container to be added to said sample void when said flexible container is squeezed, but does not allow sample in the sample void to enter into the flexible container; (i) a clip structure attached to the inner side wall of said container body as adjudged from said container body axis, said clip structure dimensioned to receive the shaft of a swab and to hold the same in position to allow for contact between the tip portion of the swab and any sample inside of said container body.

In terms of the cover and said top portion of said container body, such are preferably dimensioned to sealedly-fit with one another, such as by snap-fit. This may be down by press sealing or may in one preferred method by having the cover and said top portion of said container body being magnetically attracted to one another to allow for a sealed fit between one another. To aid opening of the cover, a tab may extend from the cover. The flexible container preferably contains viral transport medium. The viral transport medium (VTM) is selected from at least on of: universal transport medium, Eagle Minimum Essential Medium or other viral transport medium as set forth by WHO in Annex 8 (which sets for a suitable VTM for use in collecting throat and nasal swabs from human pateints as such: Add 10 g veal infusion broth and 2 g bovine albumin fraction V to sterile distilled water (t0 499 ml); add 0.8 ml gentamicin sulfate solution 50 mg·ml and 3.2 ml amphotericin B (250 ug/ml); sterilize by filtration). The straw of the collection container preferably is dimensioned to allow a patient to easily push fluid from the patient's mouth into said sample container. Wider dimensions such as ½" in diameter or more is preferable.

Clinically false negatives in the detection of SARS-CoV-2 as compared to present testing is dramatically reduced by employing multiple samples from different clinically relevant spots in the body, each with a different propensity for the virus. Mixing such samples allows for much quicker analysis than individual analysis and reduces potential processing errors in respect of the samples. In one embodiment the samples comprise saliva or sputum, and nasopharyngeal samples, both which have shown different positivity response rates, but in conjunction apparently cover all patients. Of course, additional samples, for example from pharyngeal swabs, bronchoalveolar lavage fluid specimens or fibrobronchoscope brush biopsy can be mixed in concurrently, lowering even further the possibility of a false negative. False positive are dramatically reduced by not employing amplification techniques that often lead to inactive dead virus being picked up as indicative of active viral contamination. Mass spectrometric analysis of nucleocapsid proteins is not prone to the same problem.

The specimen collection device set forth herein allows for easy sampling of fluids from patients that are independent of the patient's health. For example, saliva is much easier for patients to expectorate than sputum, especially when they are very ill while suffering from COVID-19. Nasopharyngeal samples are relatively easy to take and not very invasive. By placing the universal transport medium in a separate vessel attached to the specimen collector, patients can use a straw to help push out sample into the collection device without fear of consuming any of the universal transport medium. Alternatively, or in conjunction, other antiviral agents may be added through the flexible fluid compartment, and other flexible fluid compartments with one way valves, with conduits into the sample chamber, may be employed to add other materials to the mixed samples. The swab tip can be placed directly into the saliva or sputum and the sample mixed prior to exposure to the universal transport medium. One or more clips may be associated with the container for holding the swab shaft. As nucleocapsid proteins are quite stable at room temperature they do not need the same rigorous handling that is required for RNA based tests, such as dry ice or pretreatment.

In terms of saliva/sputum and nasopharyngeal samples positive finding of infectivity with SARS-CoV-2 is declared upon detection of amino acid sequences of at least one of: ADETQALPQR (SEQ. ID NO.: 1), DGIIWVATEGALNTPK (SEQ. ID NO.: 2), IGMEVTPSGTWLTYTGAIK (SEQ. ID NO.: 3), WYFYYLGTGPEAGLPYGANK (SEQ. ID NO.: 4) and RPQGLPNNTA SWFTALTQHG (SEQ. ID NO.: 5) with SEQ. ID NO. 5 being associated with a predominant nucleoprotein found in saliva while SEQ. ID Nos. 1-4 being associated with predominant nucleoproteins associated with nasopharyngeal samples.

In a more preferred embodiment, a positive finding of infectivity is declared only if both of SEQ. ID NO.: 1 and SEQ. ID NO.: 5 are detected as both sites are associated with a large number of ACE-2 receptors sites, one would expect a positive find in one without the other to be likely an indication of a viral artifact picked up by one of the tests. In any case, if only one of such sequences is detected, testing may be repeated via mass spectrometry, or other method, to assure in such cases that infectivity indeed exists, thus further reducing clinical false positivity.

A negative finding of infectivity is declared upon failure to detect peptide sequences of at least one of: SEQ. ID NO.:1-5.

In a preferred embodiment, before ionization saliva and/or sputum and nasopharyngeal specimens are pooled from 5 or less persons in order to improve the speed of analysis by mass spectroscopy of overall samples. Individual analysis of each specimen making up the pool is performed only if the pooled sample is found to be positive for SARS-CoV-2 by detection of at least one of SEQ. ID NO.:1-5. Such sampling technique which has not been applied to mass spectroscopy determination of viral load, should greatly reduce the time of sampling especially if the positivity rate is estimated in the sample pool to be equal to or less than 15 percent, more preferably equal to or less than 10 percent.

Also provided is a collection device for collecting sample of both saliva and/or sputum and nasopharyngeal secretions.

FIG. 1 is a prospective view of such a collection device 5. Collection device 5 is composed of a sample chamber 10 into which a biological sample form a patient is placed. Saliva sample or sputum sample may be added to chamber 10 by a patient lifting attached straw 35 by way of pulling up pull tab 40. Straw 35, found on the top part 80 of collection device 5, is retractable back into sample chamber 10 towards the bottom part 85 of collection device 5 and is held in position by retaining ring 75 held to the walls of chamber 10 by support members 30. Support members 30 have space between them to allow for the addition of a swab 45 (for example a nasopharyngeal swab), comprising a flexible shaft 50, preferably of plastic or wire, and a tip 55 preferably of synthetic material. More preferably one or more clips 70 (only one is shown) is provided along the wall of chamber 10 to allow for snapping into place swab 45 along its flexible shaft 50 thereby keeping it in place more securely (other clips may be used to snap into place other swabs such as a throat swab wherein 3 or more, 4 or more samples from distinct clinical bodily sites are to be analyzed). Shaft 50 may be broken from its clinically used full length preferably about a pre-manufactured score (not shown) to fit within collection device 5. Straw 35 is retracted back into chamber 10 after saliva and/or sputum is added to the straw 35 by the patient. Cover 30 which is affixed by joint 40 to band 25 which extends about the outside perimeter of container 10 is then placed back a reciprocally sized top portion 60 to either allow for snap coverage, magnetic coupling etc. Cover 30 may have a tab 35 extending therefrom to aid in opening and closing. Cover 30 alternatively can be separate from collection device 5, and may be a screw cap (not shown) that is complementary to threads on container 5 (not shown). With collection device 5 closed by cover 30, universal transport medium (or other reagent such as virus inactivation liquid) can be added by way of flexible pump 65 that is attached to collection device 5. Flexible pump 65 is comprised of a flexible housing 15 which when squeezed adds fluid to chamber 10 by way of conduit 20. Conduit 20 may be configured with a one-way valve to allow fluid into the chamber 10 but not into the flexible housing 14.

EXAMPLE 1

A saliva or sputum sample is collected by having a patient being tested for SARS-CoV-2 infection drool into a specimen container. Such container may be as set forth in the embodiment of FIG. 1.

At the approximately the same time a nasopharyngeal minitip swab of synthetic fiber with flexible plastic or wire shaft is placed up the nose of a patient being tested for SARS-CoV-2 infection. The minitip swab is based through the nostril parallel to the palate until resistance is encountered or the distance is equivalent to that from the ear to the nostril of the patient, indicating contact with the nasopharynx. The swab preferably reaches equal to the distance from nostrils to outer opening of the ear. The swab is gently rubbed and is rolled. The swab is left in place for several seconds to absorb secretions. The swab is removed while rotating it. Alternatively a nasal mid-tubinate swab is used with a flocked taper swab. The patient's head is tilted back approximately 70 degrees. While gently rotating the swab, the swab is inserted less than one inch (about 2 cm) into the nostril (until resistance is met at turbinates). The swab is rotated several times against the nasal wall and repeat is made in the other nostril using the same swab.

After snapping at the molded breakpoint on the swab shaft, the swab is placed into the same specimen container having the saliva or sputum sample, preferably with the swab tip in the saliva or sputum sample. The samples are commixed by upon sealing of the container by rolling, tapping, shaking etc. Viral transport medium (for example, Universal Transport Media—a room temperature stable viral transport medium) is added to the mixed specimens.

Upon receipt of samples in viral transport medium, the mixed sample is transferred to a clean polypropylene Eppendorf tube. Inactivation is by heating at 65° C. for 30 minutes in a water bath. After incubation 100% isopropanol is added to obtain a 75% solution. The sample is left to sit for 10 minutes at room temperature. The outer surface of the tubes preferably are treated with 100% isopropanol or 1% sodium hypochorite spill from a jet wash and is left to stand for 15 minutes without getting wet. Inactivated samples are cooled down to −20C for 2 hours and centrifuged at 20,000×g for 20 minutes. Alternatively ethanol precipitation can be used to concentrate proteins of the specimens conserved in the virus transport medium. The pellet is resuspended in 50 nM ammonium bicarbonate buffer, containing 0.1% Rapigest SF Surfactant (Waters) and subjected to tryptic digestion for 4 hours at 37° C. Alternatively the protein pellets are lysed by SDS, reduced, alkylated and digested by trypsin. The reaction is terminated by adding formic acid to a final concentration of 0.5%.

Peptides may be analyzed by 4 channel turbulent flow chromatography coupled to triple quadrupole MS detection. A Transcent™ TGLX-4 system with four TurboFlow Cyclone-P HPLC columns (Thermo Fisher Scientific) and four Acquity UPLC BEH C18 columns may be employed. The mobile phase for the first dimension may be 0.5% formic in water (mobile phase A), acetonitrile (mobile phase B), acetonitrile/isopropanol/acetone (40:40:20 v/v) (mobile phase C) and 20% DMSO/2% TFE in water (mobile phase D). The mobile phase for the second dimension may be 0.1% formic, 1% DMSO in water (mobile phase A) and 0.1% formic acid, and 1% DMSO in acetonitrile (mobile phase B). Tryptic digest is injected into the TurboFlow column with 0.5% formic acid in water at 1.2 mL/min. The flow is then reversed and slowed, and the retained peptide eluted and transferred onto the analytical column. The width of the transfer window is set at 96s. The TurboFlow™ Cyclone-P HPLC column is reduced of carryover by alternate flushing of the column with 20% DMSO/2% TFE in water followed by a mixture of acetonitrile/isopropanol/acetone 40:40:20 v/v. Conditions for optimizing valve switching program are determined.

A TSQ Altis Triple Quadrupole Mass Spectrometer is set for: spray voltage (kV): +4.0, sheath gas pressure: 60, auxiliary gas pressure: 15, sweep gas pressure: 2, ion transfer tube temperature (° C.): 300, vaporizer temperature (° C.): 200, Q1 Resolution (FWHM): 2.0, Q3 Resolution (FWHM): 2.0 and CID gas (mTorr): 1.5. Peptides are detected by using selected reaction monitoring at a dwell time of 100 ms per transition.

Data obtained is analyzed using PEAKS Studio 8.5 and MaxQuant version 1.6.7.0 using the following parameters: parent mass error tolerance—20 ppm, fragment mass error tolerance—0.03 Da. Up to 3 missed cleavages may be allowed but only peptides with both trypsin-specific ends are considered. Oxidation of methionine and caramidomethylation of cysteine residues may beset as possible variable modifications and up to 3 variable modifications per peptide are allowed.

The invention claimed is:

1. A method for reducing clinical false positives and negatives in the detection of SARS-CoV-2 in suspected patients employing the steps of:
   (a) mixing in a single sample container samples of collected saliva and nasopharyngeal secretions to form mixed sample;
   (b) adding universal transport medium to the mixed sample in said single sample container to form treated mixed samples;
   (c) transporting at a temperature above 0° C. the single sample container having the treated mixed samples to a remote location;
   (d) treating at such remote location the treated mixed sample to deactivate live viral content;
   (e) analyzing by one of: RT-qPCR, Immunofluorescence assays, ELISA, molecularly imprinted polymer-based detection, aptamer-based detection, and CRISPR-Cas 12-based lateral flow detection of RNA extracts, said treated and deactivated mixed sample for biological signals indicative of SARS-CoV-2 presence.

2. The method of claim 1 wherein in step (e) the biological signal is a RNA sequence unique to SARS-CoV-2.

3. The method of claim 1 wherein in step (e) the biological signal is a protein sequence unique to SARS-CoV-2.

4. The method of claim 3 wherein in step (e) the biological signal is a spike protein sequence.

5. The method of claim 3 wherein in step (e) the biological signal is a membrane protein sequence.

6. The method of claim 3 wherein in step (e) the biological signal is an envelope protein sequence.

7. The method of claim 1 wherein the mixed sample further comprises one of at least one of a: a bronchoalveolar lavage fluid sample, a throat swab sample and a fibrobronchoscope brush biopsy.

8. A method for reducing clinical false positives and negatives in the detection of SARS-CoV-2 in suspected patients employing the steps of:
   (a) mixing in a single sample container samples of collected saliva and nasopharyngeal secretions from two or more patients to form mixed sample;
   (b) adding universal transport medium to the mixed sample in said single sample container to form treated mixed samples;
   (c) transporting at a temperature above 0° C. the single sample container having the treated mixed samples to a remote location;
   (d) treating at such remote location the treated mixed sample to deactivate live viral content;
   (e) analyzing said treated and deactivated mixed sample for biological signals indicative of SARS-CoV-2 presence.

9. The method of claim 8 wherein the secretions are from five or more patients.

10. The method of claim 8 wherein the mixed sample further comprises one of at least one of a: a bronchoalveolar lavage fluid sample, a throat swab sample and a fibrobronchoscope brush biopsy.

11. The method of claim 8 wherein in step (e) the biological signal is a RNA sequence unique to SARS-CoV-2.

12. The method of claim 8 wherein in step (e) the biological signal is a protein sequence unique to SARS-CoV-2.

13. The method of claim 3 wherein in step (e) the biological signal is at least one of a spike protein sequence, a membrane protein sequence, and an envelope protein sequence.

14. A collection container for collecting saliva and/or sputum samples and specimens from a swab, said collection container comprising: (a) a container body having an open top portion and a closed bottom portion, and sidewalls encompassing a sample void, said container defined circumferentially about an axis; (b) a band of material circumferential about the sidewalls of said container body at the open top portion of said container along the outside of said sidewalls as adjudged from said container body axis; (c) a cover configured to be coupled to the top portion of the container body to close the container, said cover joined to said container body by a flexible joint adjoined to said band of material; (d) a circumferential ring about said container body axis surrounding a hole, said circumferential ring joined to the sidewalls of said container body by one or more struts; (e) a straw in said circumferential ring hole, said straw movable between a position above said top portion of said container body and a position substantially parallel to the top portion of said container body; (f) a tab extending from said straw to allow a grasping surface to pull said straw up through the circumferential ring hole and to push down said straw into said hole to a position wherein the top of the straw is substantially parallel to the top portion of said container body; (g) two or more clip structures attached to the inner side wall of said container body as adjudged from said container body axis, said clip structures dimensioned to receive the shaft of a swab and to hold the same in position to allow for contact between the tip portion of the swab and any sample inside of said container body.

15. The collection container of claim 14 wherein said cover and said top portion of said container body are dimensioned to sealedly-fit with one another.

16. The collection container of claim 14 wherein said flexible container contains viral transport medium.

17. The collection container of claim 16 wherein the viral transport medium is selected from at least on of: universal transport medium, or other viral transport medium approved by the World Health Organization.

18. The collection container of claim 14 wherein the straw is dimensioned to allow a patient to push fluid from the patient's mouth into said sample container.

19. The collection container of claim 14 wherein the clip structure is configured for fitting the shaft of a nasopharyngeal swab used in SARS-CoV-2 screening.

20. The collection container of claim 14 wherein the sample void of the container body is dimensioned to allow for between 0-5 ml of saliva to be tested for SARS-CoV-2.

* * * * *

SEQUENCE LISTING

```
<160> NUMBER OF SEQ ID NOS: 5

<210> SEQ ID NO 1
<211> LENGTH: 10
<212> TYPE: PRT
<213> ORGANISM: Severe accute respiratory syndrome coronavirus 2

<400> SEQUENCE: 1

Ala Asp Glu Thr Gln Ala Leu Pro Gln Arg
1               5                   10

<210> SEQ ID NO 2
<211> LENGTH: 16
<212> TYPE: PRT
<213> ORGANISM: Severe acute respiratory syndrome coronavirus 2

<400> SEQUENCE: 2

Asp Gly Ile Ile Trp Val Ala Thr Glu Gly Ala Leu Asn Thr Pro Lys
1               5                   10                  15

<210> SEQ ID NO 3
<211> LENGTH: 19
<212> TYPE: PRT
<213> ORGANISM: Severe acute respiratory syndrome coronavirus 2

<400> SEQUENCE: 3

Ile Gly Met Glu Val Thr Pro Ser Gly Thr Trp Leu Thr Tyr Thr Gly
1               5                   10                  15

Ala Ile Lys

<210> SEQ ID NO 4
<211> LENGTH: 20
<212> TYPE: PRT
<213> ORGANISM: Severe acute respiratory syndrome coronavirus 2

<400> SEQUENCE: 4

Trp Tyr Phe Tyr Tyr Leu Gly Thr Gly Pro Glu Ala Gly Leu Pro Tyr
1               5                   10                  15
```

-continued

```
Gly Ala Asn Lys
            20

<210> SEQ ID NO 5
<211> LENGTH: 20
<212> TYPE: PRT
<213> ORGANISM: Severe acute respiratory syndrome coronavirus 2

<400> SEQUENCE: 5

Arg Pro Gln Gly Leu Pro Asn Asn Thr Ala Ser Trp Phe Thr Ala Leu
1               5                   10                  15

Thr Gln His Gly
            20
```